United States Patent [19]

Mais et al.

[11] Patent Number: 4,925,994
[45] Date of Patent: May 15, 1990

[54] PROCESS FOR THE RING CHLORINATION OF AROMATIC HYDROCARBONS

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 342,500

[22] Filed: Apr. 24, 1989

[30] Foreign Application Priority Data

May 6, 1988 [DE] Fed. Rep. of Germany ....... 3815537
Jul. 15, 1988 [DE] Fed. Rep. of Germany ....... 3824068

[51] Int. Cl.$^5$ .................................. C07C 17/12
[52] U.S. Cl. .................................. 570/210; 540/455; 540/468; 570/207; 570/208; 570/209
[58] Field of Search ............... 540/468, 455; 570/207, 570/208, 209, 210

[56] References Cited

FOREIGN PATENT DOCUMENTS 0126669 11/1984 European Pat. Off. ........... 570/206
0292824 11/1988 European Pat. Off. ........... 570/206

*Primary Examiner*—Werren B. Lone
*Attorney, Agent, or Firm*—Sprung, Horn, Kramer & Woods

[57] ABSTRACT

Aromatic hydrocarbons which are monosubstituted by straight-chain or branched $C_1$–$C_{12}$-alkyl or by $C_3$–$C_8$-cycloalkyl can be chlorinated in the presence of Friedel-Crafts Catalysts in liquid phase on the aromatic ring if 1,6-benzothiazocins are used as co-catalysts. This makes it possible to obtain a higher proportion of p-isomers.

20 Claims, No Drawings

PROCESS FOR THE RING CHLORINATION OF AROMATIC HYDROCARBONS

BACKGROUND OF THE INVENTION

The invention relates to a process for the ring chlorination of aromatic hydrocarbons in the presence of Friedel-Crafts catalysts and in the presence of co-catalysts in liquid phase.

The reaction of aromatic hydrocarbons, such as toluene, in liquid phase with chlorine gas to give ringsubstituted chlorinated derivatives, such as monochlorotoluene, is known (Ullmanns Enzyklopädie der technischen Chemie (Ullmann's Encyclopaedia of Industrial Chemistry), 4th edition, Volume 9, page 449 f.). In general this chlorination is carried out in the presence of Friedel-Crafts catalysts, such as iron(III) chloride, antimony chlorides or aluminium chloride. The chlorination product obtained is usually a mixture of isomeric monochlorinated and polychlorinated compounds. If FeCl$_3$ is used, for example, a mixture of monochlorotoluenes and dichlorotoluenes is obtained from toluene; the main product of the monochlorotoluene fraction is o-chlorotoluene beside p-chlorotoluene and a small amount of m-chlorotoluene.

Since especially p-chloroalkylbenzenes, such as p-chlorotoluene, are useful intermediates, there has not been a lack of attempts in the past to control the chlorination in such a manner that the ratio of o- to p-chloroalkylbenzene is lowered, that is, the attempt is made to find conditions within favour the formation of p-chloroalkylbenzenes.

It is known from U.S. Pat. No. 3,226,447 that by the addition of sulphur compounds having divalent sulphur to the Friedel-Crafts catalyst an o/p ratio of 1.2 can be obtained in the chlorination of toluene. The disadvantage of this process resides in the fact that this less than favourable ratio can only be achieved if antimony salts are used as Friedel-Crafts catalysts. Another disadvantage is that the required amount of the catalyst components according to Example 16 of that application are very high, specifically 1% by weight for each of the two catalytic additives. As shown by the o/p ratio having a value of >1, the result is still more o- than p-chlorotoluene.

DE-OS (German Published Specification) 1,543,020 and U.S. Pat. No. 4,031,144 also describe the chlorination of toluene, for example, with FeCl$_3$ and S$_2$Cl$_2$. The ratio obtained of o/p=1.03–1.10 is still unsatisfactorily high.

U.S. Pat. No. 4,031,147, U.S. Pat. No. 4,069,263, U.S. Pat. No. 4,069,264 and U.S. Pat. No. 4,250,122 describe the chlorination of toluene with Friedel-Crafts catalysts with the addition of thianthrenes of substituted thianthrenes. The most favourable o/p ratios obtainable are around 0.7, which, however, are only obtained either by using antimony salts or, if iron salts are used, only at very low reaction temperatures of about 0° C. Both situations are extremely unfavourable for practical application. Thus, the co-catalytic action of the thianthrenes in combination with the use of antimony salts is greatly impaired by traces or iron, which is difficult to avoid in practice. In addition the reaction is strongly exothermic to such an extent that removal of the heat at about 0° C. by ice/salt cooling becomes very expensive. The thianthrenes are furthermore destroyed under conventional reaction conditions even by the everpresent traces of water and thus lose their efficiency.

Furthermore, U.S. Pat. No. 4,289,916, EP 63,384 and EP 173,222 disclose the chlorination of toluene in the presence of Lewis acids and phenoxathiines. The o/p ratio of 0.6 obtainable according to Example 1 from EP 173,222 is again achieved only by the use of antimony chloride and the high amount of 0.29% by weight of co-catalyst, which are extremely unfavourable for practical application. By using FeCl$_3$ instead of antimony chloride, an o/p ratio of 0.68 is obtained, but again only at a low reaction temperature of 5° C., which is extremely unfavourable for practical application. At a reaction temperature of 50° C., which is advantageous for practical application, the o/p ratio increases to 0.88 in the presence of FeCl$_3$ and the phenoxathiine derivative claimed in EP 173,222, as shown by experiments which we carried out (cf. Example 21). U.S. Pat. No. 4,289,916 and EP 63,384 mentioned describe a favourable o/p ratio of about 0.8. In this case, too, the o/p ratio can be lowered to 0.65 by using, instead of FeCl$_3$, antimony chloride and a reaction temperature of 20° C., that is, unfavourable conditions for practical application. In addition, phenoxathiines are destroyed in the presence of traces of water.

EP 126,669 discloses the chlorination of toluene in the presence of Friedel-Crafts catalysts and N-substituted phenothiazines. In this case, too, the o/p ratio of 0.84 is unfavorably high.

EP 112,722, EP 154,236 and EP 248,931 disclose the chlorination of toluene in the presence of certain zeolites, in which an o/p ratio of about 0.3 is achieved if, for example, halocarboxylic acid halides are added as moderators. The disadvantages of this process are the substantial amounts of 5% by weight of zeolite and 1% by weight of moderators. As our own experiments have shown, this result must be paid for by the substantial disadvantage that very large amounts (up to 8% by weight) of benzyl chlorides are formed in the mixtures obtained. The formation of benzyl chlorides interferes in the subsequent conventional workup by distillation quite extensively.

SUMMARY OF THE INVENTION

A process has now been found for the ring chlorination of aromatic hydrocarbons of the formula

 (I)

in which

R denotes straight-chain or branched C$_1$-C$_2$-alkyl or C$_3$-C$_8$-cycloalkyl in the presence of Friedel-Crafts catalysts and in the presence of co-catalysts in liquid phase, which is characterized in that co-catalysts used are 1,6-benzothiazocins.

DETAILED DESCRIPTION OF THE INVENTION

The skeleton of the 1,6-benzothiazocins is represented by the following formula and the numbering:

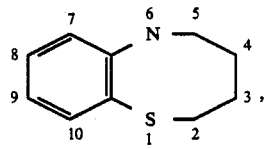

(II)

The 1,6-benzothiazocins for the process according to the invention can be characterized by the following formula

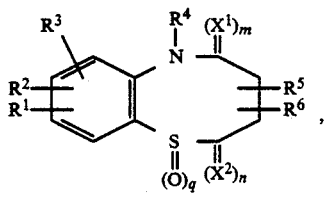

(III)

in which

R¹ and R², independently of one another, denote hydrogen hydroxyl, amino, cyano, halogen, nitro, alkylsulphonyl, phenylsulphonyl, alkylsulphoxyl, phenylsulphoxyl, tosyl, mercapto, carboxyl, halocarbonyl, carboxyamide, alkoxycarbonyl, thiocarboxyamide, alkyl, aryl, heteroaryl, alkoxy, aryloxy, heteroaryloxy, acyloxy, alkylthio, arylthio, heteroarylthio, acylthio, acyl, thioacyl or acylamino, R³ stands for hydrogen or chlorine and can further form a fused saturated, unsaturated or aromatic isocyclic or heterocyclic 5- to 8-membered ring with one of the radicals R¹ or R² and together with the substituted carbon atoms, R⁴ denotes hydrogen, halocarbonyl, alkyl, aryl, heteroaryl, acyl, thioacyl or alkoxycarbonyl, X¹ and X², independently of one another, stand for doubly bound oxygen, sulphur or R⁷-substituted nitrogen, R⁷ having the range of meaning of R⁴ with the exception of hydrogen, m, n and o, independently of one another, can adopt the value 0 or 1 and R⁵ and R⁶, independently of one another, can be located on one or two of the carbon atoms between the S and N atom in the 8-membered ring, unless these carbon atoms are occupied by X¹ or X², and have the range of meaning of R¹ and R², where in the case of vicinal substitution they can also form a saturated, unsaturated or aromatic isocyclic or heterocyclic 5- to 8-membered ring with the substituted carbon atoms and where furthermore they can adopt the range of meaning of the doubly bound oxygen or sulphur.

Examples of halogens are fluorine, chlorine, bromine or iodine, preferably fluorine, chlorine or bromine, particularly preferably fluorine or chlorine.

Suitable alkyl radicals in the substituents mentioned are open-chain radicals having 1–16 carbon atoms, preferably 1–4 carbon atoms, and cyclic radicals having 5–8 carbon atoms, preferably 5 or 6 carbon atoms. These alkyl radicals can themselves be substituted by $C_1$–$C_4$-alkyl, preferably methyl or ethyl, thus arriving at the series of branched alkyl radicals. These alkyl radicals can furthermore be monosubstituted or polysubstituted by fluorine, chlorine or bromine. These alkyl radicals can furthermore be substituted by $C_1$–$C_4$-alkoxy, preferably methoxy or ethoxy, thus arriving at the ether series. These alkyl radicals can furthermore be substituted by phenyl, naphthyl or biphenyl, thus arriving at the series of aralkyl radicals. Examples of such alkyl radicals are: methyl, ethyl, propyl, isopropyl, butyl, isobutyl, tert.-butyl, amyl, hexyl, octyl, decyl, dodecyl, hexadecyl, cyclopentyl, methylcyclopentyl, cyclohexyl, methylcyclohexyl, cycloheptyl, cyclooctyl, methoxymethyl, ethoxymethyl, benzyl, phenylethyl, chloromethyl, dichloromethyl, trichloromethyl, trifluoromethyl; particularly important radicals are, for example, methyl, ethyl, n-propyl, benzyl and trifluoromethyl.

The range of meaning mentioned for alkyl radicals applies in principle also to alkoxy and alkylthio; radicals having 1–6 carbon atoms are preferred, those having 1–4 carbon atoms, such as methoxy, ethoxy, tert.-butoxy, cyclohexyloxy, trifluoromethoxy, methylthio, ethylthio, cyclohexylthio, trifluoromethylthio and trichloromethylthio are particularly preferred.

Examples of suitable aryl radicals in the above substituents are phenyl, naphthyl or biphenyl, which themselves can be substituted by fluorine, chlorine, bromine, nitro, $C_1$–$C_4$-alkyl or $C_1$–$C_4$-alkoxy, for example phenyl, naphthyl, tolyl, anisyl, chlorophenyl, nitrophenyl; for example, phenyl and chlorophenyl and particularly important.

Suitable heteroaryl radicals in the above substituents are those having 5–9 carbon atoms, preferably 5 or 6 carbon atoms and having 1–3, preferably 1 or 2, particularly preferably 1, heteroatoms in the ring. They can be aromatic or nonaromatic, but preferably they are aromatic. These heteroaryl radicals themselves can be substituted by methyl, ethyl, fluorine or chlorine. Examples are: pyridyl, methylpyridiyl, furyl, pyrrolyl, and imidazolyl.

What has been said above with respect to the alkoxy and alkylthio radicals applies analogously to the aryloxy, heteroaryloxy, arylthio and heteroarylthio radicals.

Acyl radicals within the above substituents have 2–8 carbon atoms and are aliphatic, preferably having 2–4 carbon atoms, or given the necessary number of carbon atoms, aromatic. They can themselves be substituted by a second substituent from those mentioned above for alkyl radicals and aryl radicals. Examples are: acetyl, chloroacetyl, trichloroacetyl, trifluoroacetyl, benzoyl, chlorobenzoyl, chlorocarbonyl, formyl.

In the case where R³ forms a ring with one of the radicals R¹ or R² and together with the substituted carbon atoms, this ring can be isocyclic and saturated, unsaturated or aromatic or even be heterocyclic by containing N, O and/or S atoms. Rings of this type have 5–8, preferably 5 or 6, ring members and are fused onto the benzene ring shown in formula (III). Examples are: benzo, naphthalino, thieno, furano, pyrrolo, pyridino, cyclohexano, cyclopentano, oxolano, dioxolano, and preferably benzo and cyclohexano.

The following list which is by no means exhaustive serves as illustration for 1,6-benzothiazocins to be used according to the invention:

3,4-Dihydro-2H-1,6-benzothiazocin-5(6H)-one,
3,4-Dihydro-2H-1,6-benzothiazocin-5(6H)-thione,
4-Acetyl-3,4-dihydro-2H-1,6-benzothiazocin-5(6H)-one,
4-Methyl-3,4-dihydro-2H-1,6-benzothiazocin-5(6H)-one,
3-Methyl-3,4-dihydro-2H-1,6-benzothiazocin-5(6H)-one, 2-Methyl-3,4-dihydro-2H-1,6-benzothiazocin-5(6H)-one,
2-Ethyl-3,4-dihydro-2H-1,6-benzothiazocin-5(6H)-one,
2-Propyl-3,4-dihydro-2H-1,6-benzothiazocin-5(6H)-one,
2-Phenyl-3,4-dihydro-2H-1,6-benzothiazocin-5(6H)-one,
4-Methyl-4-acetyl-3,4-dihydro-2H-1,6-benzothiazocin-5(6H)-one,
2,4-Dimethyl-3,4-dihydro-2H-1,6-benzothiazocin-5(6H)-one,
3,4-Tetramethylene-3,4-dihydro-2H-1,6-benzothiazocin-5(6)-one,
2,3-Tetramethylene-3,4-dihydro-2H-1,6-benzothiazocin-5(6H)-one,
2,3-Tetramethylene-5,6-dihydro-2H-1,6-benzothiazocin-4(3H)-one,
2,3-Tetramethylene-3,4,5,6-tetrahydro-2H-1,6-benzothiazocin,
3,4,5,6-Tetrahydro-2H-1,6-benzothiazocin,
6-Acetyl-3,4,5,6-tetrahydro-2H-1,6-benzothiazocin,
6-Trifluoroacetyl-3,4,5,6-tetrahydro-2H-1,6-benzothiazocin,
6-Chloroacetyl-3,4,5,6-tetrahydro-2H-1,6-benzothiazocin,
6-Methyl-3,4,5,6-tetrahydro-2H-1,6-benzothiazocin,
6-Ethyl-3,4,5,6-tetrahydro-2H-1,6-benzothiazocin,
6-Acetyl-3,4-dihydro-2H-1,6-benzothiazocin-5(6H)-one,
6-Trifluoroacetyl-3,4-dihydro-2H-1,6-benzothiazocin-5(6H)-one,
6-Chloroacetyl-3,4-dihydro-2H-1,6-benzothiazocin-5(6H)-one,
6-Methyl-3,4-dihydro-2H-1,6-benzothiazocin-5(6H)-one,
6-Benzyl-3,4-dihydro-2H-1,6-benzothiazocin-5(6H)-one,
2H-Benzothiazocin-3(4H)-5(6H)-dione,
2H-3,4-dihydro-1,6-benzothiazocin-2,5(6H)-dione,
8-Chloro-3,4-dihydro-2H-1,6-benzothiazocin-5(6H)-one,
8-Methyl-3,4-dihydro-2H-1,6-benzothiazocin-5(6H)-one,
8-Methoxy-3,4-dihydro-2H-1,6-benzothiazocin-5(6H)-one,
9-Methoxy-3,4-dihydro-2H-1,6-benzothiazocin-5(6)-one,
8-Methoxy-2,3-tetramethylene-3,4-dihydro-2H-1,6-benzothiazocin-5(6H)-one,
8-Fluoro-3,4-dihydro-2H-1,6-benzothiazocin-5(6)-one,
2,3-Dimethyl-3,4-dihydro-2H-1,6-benzothiazocin-5(6H)-one,
2,3-Dimethyl-6-acetyl-3,4-dihydro-2H-1,6-benzothiazocin-5(6H)-one,
8,9-Dimethyl-3,4-dihydro-2H-1,6-benzothiazocin-5(6H)-one,
8,10-Dimethyl-3,4-dihydro-2H-1,6-benzothiazocin-5(6H)-one,
8,10-Dimethyl-3,4,5,6-tetrahydro-2H-1,6-benzothiazocin,
8,10-Dimethyl-2,3-tetramethylene-3,4-dihydro-2H-1,6-benzothiazocin-5(6H)-one,
8,10-Dimethyl-3,4-dihydro-2H-1,6-benzothiazocin-5(6H)-thione,
8,10-Dimethyl-2,3-tetramethylene-3,4-dihydro-2H-1,6-benzothiazocin-5(6H)-thione,
8-Methyl-3,4-dihydro-2H-1,6-benzothiazocin-5(6H)-thione,
8-Trifluoromethyl-3,4-dihydro-2H-1,6-benzothiazocin-5(6H)-one,
2-Chloro-3,4-dihydro-2H-1,6-benzothiazocin-5(6H)-one,
2,2-Dimethyl-3,4-dihydro-2H-1,6-benzothiazocin-5(6H)-one,
1-Oxo-3,4-dihydro-2H-1,6-benzothiazocin-5(6H)-one,
1-Oxo-3,4,5,6-tetrahydro-2H-1,6-benzothiazocin,
2H-1,6-Dibenzo[b,f]thiazocin-5(6H)-one,
5,6-Dihydro-2H-1,6-benzo[b,f]thiazocin and
3,4-Dihydro-2H-1,6,2,3-naphtalenethiazocin-5(6H)-one, preferably:
3,4-Dihydro-2H-1,6-benzothiazocin-5(6H)-one,
2-Methyl-3,4-dihydro-2H-1,6-benzothiazocin-5(6H)-one,
2,4-Dimethyl-3,4-dihydro-2H-1,6-benzothiazacin-5(6H)-one,
3,4-Tetramethylene-3,4-dihydro-2H-1,6-benzothiazocin-5(6H)-one,
2,3-Tetramethylene-3,4-dihydro-2H-1,6-benzothiazocin-5(6H)-one,
2,3-Tetramethylene-3,4,5,6-tetrahydro-2H-1,6-benzothiazocin,
3,4,5,6-Tetrahydro-2H-1,6-benzothiazocin,
6-trifluoroacetyl-3,4,5,6-tetrahydro-2H-1,6-benzothiazocin,
6-Acetyl-3,4-dihydro-2H-1,6-benzothiazocin-5(6H)-one,
6-Methyl-3,4-dihydro-2H-1,6-benzothiazocin-5(6H)-one,
8-Methyl-3,4-dihydro-2H-1,6-benzothiazocin-5(6H)-one,
6-Acetyl-3,4,5,6-tetrahydro-benzothiazocin,
2-Phenyl-3,4-dihydro-2H-1,6-benzothiazocin-5(6H)-one,
4-Methyl-3,4-dihydro-2H-1,6-benzothiazocin-5(6H)-one,
8-Methoxy-3,4-dihydro-2H-1,6-benzothiazocin-5(6H)-one,
8-Methoxy-2,3-tetramethylene-3,4-dihydro-2H-1,6-benzothiazocin-5(6H)-one,
2,3 -Dimethyl-3,4-dihydro-2H-1,6-benzothiazocin-5(6H)-one,
8,10-Dimethyl-3,4-dihydro-2H-1,6-benzothiazocin-5(6H)-one,
8,10-Dimethyl-3,4,5,6-tetrahydro-2H-1,6-benzothiazocin,
8,10-Dimethyl-2,3-tetramethylene-3,4-dihydro-2H-1,6-benzothiazocin-5(6H)-one and
3,4-Dihydro-2H-1,6-benzothiazocin-5(6H)-thione.

Preferred 1,6-benzothiazocins are those of the formulae

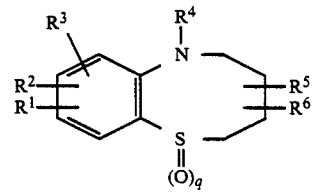

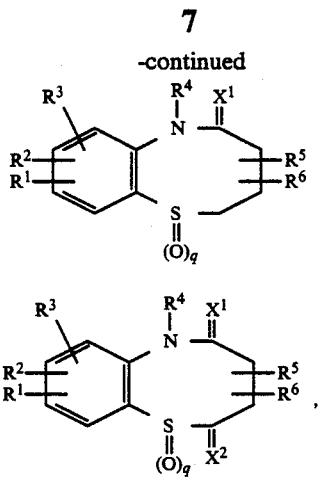

in which
R$^1$ to R$^6$, X$^1$, X$^2$ and o have the abovementioned range of meaning.

1,6-Benzothiazocins of the formulae (IV) and (V) are particularly preferably used.

1,6-Benzothiazocins of the formula (V) are very particularly preferably used.

1,6-Benzothiazocins of the formula (III) in which the index o has the value zero are also preferably used.

1,6-Benzothiazocins of the formula (III) in which the radicals R$^{11}$, R$^{12}$ and R$^{13}$ take the place of R$^1$, R$^2$ and R$^3$, of which R$^{11}$ and R$^{12}$, independently of one another, denote hydrogen, halogen, nitro, alkyl, aryl, alkoxy, aryloxy, acyloxy, alkylthio, arylthio, acyl or thioacyl and R$^{13}$ stands for hydrogen or chlorine and can further form a fused saturated isocyclic 5- or 7-membered ring or a fused benzene ring with one of the radicals R$^{11}$ and R$^{12}$ and together with the substituted carbon atoms, are also preferably used.

1,6-Benzothiazocins of the formula (III) in which the radicals R$^{21}$, R$^{22}$ and R$^{23}$ take the place of R$^{11}$, R$^{12}$ and R$^{13}$, of which R$^{21}$ or R$^{22}$, independently of one another, denote hydrogen, C$_1$–C$_4$-alkyl, C$_1$–C$_4$-alkoxy, fluorine or chlorine and R$^{23}$ stands for hydrogen or chlorine and can further form a fused cyclopentane, cyclohexane or benzene ring with one of the radicals R$^{21}$ or R$^{22}$ and together with the substituted carbon atoms, are very particularly preferred.

Further preferred 1,6-benzothiazocins are those of the formula (III) in which the radical R$^{14}$ denoting hydrogen, C$_1$–C$_4$-alkyl, phenyl, C$_1$–C$_4$-acyl or C$_2$–C$_4$-alkoxycarbonyl takes the place of R$^4$. Those 1,6-benzothiazocins of the formula (III) in which the radical R$^{24}$ denoting hydrogen, C$_1$–C$_2$-alkyl, benzyl, phenyl, formyl, acetyl, trifluoroacetyl, chlorocarbonyl, or propionyl takes the place of R$^{14}$ are particularly preferred.

Further preferred 1,6-benzothiazocins are those of the formula (III) in which the radicals R$^{15}$ and R$^{16}$ denoting hydrogen, C$_1$–C$_4$-alkyl, C$_1$–C$_4$-alkoxy, C$_1$–C$_4$-acyl, phenyl, fluorine or chlorine and where furthermore both radicals can form a cyclopentane, cyclohexane or benzene ring together with the substituted carbon atoms in the case of vicinal substitution take the place of R$^5$ and R$^6$.

The 1,6-benzothiazocins to be used according to the invention can be prepared by known processes, for example by reaction of substituted or unsubstituted aminothiophenoles with γ-butyrolactones (DE-AS (German Published Specification) 1,545,805, DE-AS (German Published Specification) 1,545,806, U.S. No. 3,155,649) or by ring enlargement of benzothiepines (GB 1,112,681, U.S. No. 3,311,615).

Examples of the aromatic hydrocarbons of the formula (I) to be chlorinated on the ring according to the invention are: toluene, ethylbenzene, propylbenzene, cumene, tert.-butylbenzene and phenylcyclohexane; the process is particularly important for the ring chlorination of toluene.

The process according to the invention is carried out in liquid phase, in which the aromatic hydrocarbon can be used in liquid (melted) form or, if desired, diluted with an inert solvent. Suitable solvents are those which are not attacked by chlorine under the conditions of a ring chlorination and are known to one skilled in the art, for being resistant, such as methylene chloride, chloroform, carbon tetrachloride and acetic acid. Preferably, no solvent is used.

The chlorinating agent for the process according to the invention is preferably chlorine. The chlorine can be passed into the reaction mixture as a liquid or a gas. Preferably, gaseous chlorine is used. However, it is also possible to use other chlorinating agents which, such as, for example, sulphuryl chloride, release chlorine under the reaction conditions. The water content of the reaction mixture is not critical, in principle, as far as the employed Friedel-Crafts catalyst is not completely deactivated. Insorfar it is preferred to not specifically dry the starting materials but to employ the same in the state in which they usually occur in the practice of technical chemistry. However, it is also possible, according to the invention to dry some or all of the starting compounds. In general the water content should not be above the saturation limits of the starting compounds. Preferably the water content of the reaction mixture is up to 250 ppm, especially preferably up to 150 ppm, and very especially preferably up to 100 ppm.

The ring chlorination to be carried out according to the invention can in principle be carried out at a temperature from the solidification point to the boiling point of the reaction mixture. In general the reaction temperature is 0°–100° C., preferably 20°–80° C., particularly preferably 40°–60° C.

The reaction pressure can be atmospheric, reduced or superatmospheric pressure and it is principle not critical. Operation at atmospheric pressure is preferred because of the low costs. Superatmospheric pressure may be advisable, for example, if the reaction is carried out above the boiling point of a low-boiling solvent; in this case, it is possible, for example, to carry out the reaction under the automatically resulting internal pressure of the reaction mixture. The chlorination degree of the reaction mixture is preferably not higher than 1, relative to the aromatic hydrocarbon to be chlorinated. Higher chlorination degrees are possible, but usually not advantageous, since they lead to the formation of undesired polychlorinated products. Chlorine or a chlorine-releasing substance is therefore used, for example, in an amount of 0.8–1.1, preferably 0.8–1.0, mole per mole of the aromatic hydrocarbon.

Friedel-Crafts catalysts for the process according to the invention are all those known, for example antimony chlorides, antimony oxychloride, aluminium chloride, iron(II) chloride, iron(III) chloride, tellurium chlorides, molybdenum chlorides, tungsten chlorides, titanium chlorides, zinc chloride, tin chlorides, boron chloride and/or boron trifluoride. However, it is also possible to use elements and compounds of elements which form a Friedel-Crafts catalysts (Lewis acid) during the chlorination. For example, the elemental metals or the semi-metals antimony, iron, lead, tin, zinc, molybdenum, tellurium and aluminium or their oxides, sulphides, carbonyls or salts (for example carbonates or the like); examples are antimony oxides, iron oxides, iron sulphides, lead sulphides, tin sulphides, zinc sulphides, iron carbonyls, molybdenum carbonyls and/or boron phosphate. Instead of the chlorides mentioned, the bromides, optionally also the fluorides or iodides, of the elements mentioned can be used. Preferred Friedel-Crafts catalysts are antimony chlorides, aluminium chlorides, iron, iron oxides, iron sulphides, iron carbonyls and/or iron(III) chloride. Iron (III) chloride is particularly preferred.

The amounts of the Friedel-Crafts catalyst of a mixture of several of them can be varied within wide limits. Thus, a catalytic effect is already detectable with an addition of 0.0005% by weight; on the other hand, it is also possible to add 5% by weight or more of the Friedel-Crafts catalyst, but such large amounts usually do not offer any advantage, and instead may lead to difficulties during the workup. Usually the Friedel-Crafts catalyst is used in an amount of 0.001–0.5% by weight, preferably 0.01–0.1% by weight. All amounts stated are based on the amount of the aromatic hydrocarbon used.

The co-catalysts usable according to the invention comprise, in addition to the abovementioned substances, all substances which are capable under the reaction conditions of forming mixtures of compounds which are covered by the abovementioned formula (III) to (VI). They are, for example, those compounds which are mono-unsaturated or polyunsaturated. Furthermore, they are open-chain precursors which undergo ring closure under the conditions according to the invention and thus are converted into co-catalysts according to the invention. Furthermore, all substances which can be formed under the reaction conditions of chlorination by reaction of the abovementioned co-catalysts according to the invention with chlorine or hydrogen chloride can be used. Examples are the hydrochlorides of the abovementioned co-catalysts.

It is furthermore possible to use the co-catalysts combination with other elements or compounds which are not claimed as co-catalysts in the process according to the invention. The co-catalysts can be used not only individually but also in a mixture of several of them. The amounts in which the co-catalysts according to the invention can be used can vary within wide limits. However, amounts under 0.0001% by weight are less advantageous, since in this case the co-catalytic action diminishes. It is even possible to add amounts of 5% by weight of more of co-catalyst, but these large amounts in general do not offer any advantage and instead may lead to difficulties during the workup. The co-catalysts according to the invention are therefore in general used in an amount of 0.0001–0.5% by weight, preferably 0.0005–0.1% by weight, particularly preferably 0.0005–0.0075% by weight, relative to the aromatic hydrocarbon used.

The molar ratio of the mixture of Friedel-Crafts catalyst(s) and co-catalyst(s) can be varied within wide limits in the process according to the invention. In general it is advantageous not to use too large an excess of the co-catayst with respect to the Friedel-Crafts catalyst. Likewise it is in general more advantageous not to choose a too large excess of the Fiedel-Crafts catalyst. According to the invention, a molar ratio of Friedel-Crafts catalyst to co-catalyst is 100:1–1:10, preferably 75:1–4, particularly preferably 50:1–1:2.

When the process according to the invention is carried out in practice, the individual components of the reaction mixture are added in any desired order. This process can be carried out both continuously and batchwise. An exemplary embodiment is as follows: The desired aromatic hydrocarbon, for example toluene, is initially introduced and brought to the desired temperature (for example 50° C.). The desired amount of Friedel-Crafts catalyst(s) and co-catalyst(s) are added in any desired order and, while keeping the temperature essentially constant, chlorine gas is introduced until the desired chlorination degree has been reached. The mixture is then worked up in a conventional manner by distillation.

A further exemplary embodiment is as follows: A mixture of alkylbenzene containing the desired amounts of catalyst and co-catalyst is prepared and brought to the desired reaction temperature. The chlorinating agent is then introduced until the desired chlorination degree has been reached. The workup can in this case also be carried out in a conventional manner by distillation.

A further embodiment is as follows:

A solution of catalyst and co-catalyst in the alkylbenzene is prepared and transferred to a continuously operating chlorinating apparatus. Likewise a chlorinating agent is introduced continuously at such a rate that the desired chlorination degree is reached. In this case, too, the reaction mixture being formed continuously can be worked up in a conventional manner by distillation.

In contrast to the process according to the invention, the previously known heterocycles for controlling the o/p selectivity always had a different structure, that is to say, the form of three linearly fused 6-membered rings.

In the process according to the invention, it is surprising that the co-catalysts according to the invention have such a distinct selecting effect on the o/p ratio, with the result that predominantly the p-compound is formed. Furthermore, the fact that the co-catalysts according to the invention yield such good results especially in combination with the Friedel-Crafts catalyst $FeCl_3$ which is extremely favourable and desirable for practical application is particularly surprising and extremely advantageous.

Another surprising fact is that these good results are achieved at temperatures, for example in the range of 40°–60° C., which are very advantageous in terms of practical application. Still another surprising fact is that the co-catalysts according to the invention exhibit their p-selective action even at extremely low concentrations so that the required amounts of co-catalysts are particularly small. Thus, they are in the particularly preferred range of 0.0005–0.0075% by weight, which is powers of ten less than in the case of the previously known co-catalysts.

This fact is extremely advantageous In terms of practical application as well as ineconomical and ecological terms. In a further favourable manner, the co-catalyst according to the invention can be prepared in a simple manner by a single reaction step from commercially available starting materials.

EXAMPLE 1

100 parts by weight of toluene were initially introduced into a reactor with stirring, and 0.017 part by weight of FeCl₃ and 0.0045 parts by weight of the co-catalyst of the formula

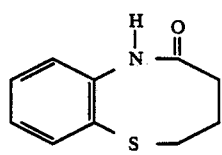

(3,4-dihydro-2H-1,6-benzothiazocin-5(6H)-one) was added and the mixture was heated to 50° C. While maintaining the temperature essentially constant, 93–95 mol % of chlorine, relative to toluene, was uniformly introduced as a gas over a period of 5 hours. The residual toluene content in the reaction mixture was 4.3% by weight and the ratio of ortho-chlorotoluene to para-chlorotoluene (o/p) was 0.80.

EXAMPLE 2

The procedure of Example 1 was repeated. However, 0.0045 part by weight of the co-catalyst of the formula

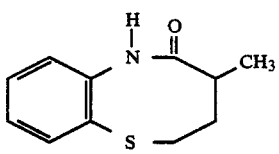

(4-methyl-3,4-dihydro-2H-1,6-benzothiazocin-5(6H)-one) was added. The residual toluene content was 4.6% and the o/p ratio 0.94.

EXAMPLE 3

The procedure of Example 1 was repeated, except that 100 parts by weight of ethylbenzene were used instead of toluene. The residual ethylbenzene content was 10.6% by weight and the ratio of ortho-chloroethylbenzene to para-chloroethylbenzene was o/p=0.69.

EXAMPLE 4

The procedure of Example 1 was repeated, except that 100 parts by weight of cumene were used instead of toluene. The residual cumene content was 11.7% by weight and the ratio of ortho-chloroisopropylbenzene to parachloroisopropylbenzene was o/p=0.41.

EXAMPLE 5

The procedure of Example 1 was repeated, except that 100 parts of weight by cyclohexylbenzene were used instead of toluene. The residual cyclohexylbenzene content was 10.8% by weight and the ratio of ortho-chlorocyclohexylbenzene to para-chlorocyclohexylbenzene was o/p=0.44.

EXAMPLE 6

The procedure of Example 1 was repeated, except that 100 parts by weight of t.-butylbenzene were used instead of toluene. The residual tert.-butylbenzene content was 10.3% by weight and the ratio of ortho- to parachloro-t.-butylbenzene was o/p=0.22.

EXAMPLE 7

The procedure of Example 1 was repeated. However, 0.005 part by weight of the co-catalyst of the formula

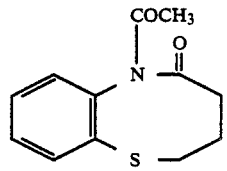

(6-acetyl-3,4-dihydro-2H-1,6-benzothiazocin-5(6H)-one was added. The residual toluene content was 4.2% by weight and the o/p ratio was o/p=0.90.

EXAMPLE 8

The procedure of Example 1 was repeated. However, 0.0045 part by weight of the co-catalyst of the formula

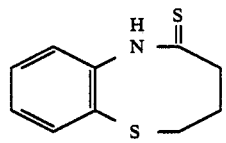

(3,4-dihydro-2H-1,6-benzothiazocin-5(6H)-thione) was added. The residual toluene content was 3.5% by weight and the o/p ratio 1.00.

EXAMPLE 9

The procedure of Example 1 was repeated. However, 0.005 part by weight of the co-catalyst of the formula

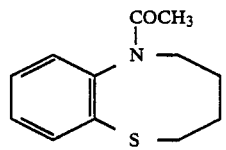

(6-acetyl-3,4,5,6-tetrahydrothiazocin) was added. The residual toluene content was 4.1% by weight and the o/p ratio 0.93.

EXAMPLE 10

The procedure of Example 1 was repeated. However, 0.0061 part by weight of the co-catalyst of the formula

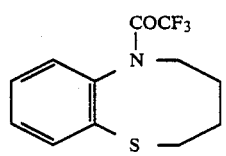

(6-trifluoroacetyl-3,4,5,6-tetrahydro-2H-1,6-benzothiazocin) was added. The residual toluene content was 3.3% by weight and the o/p ratio was 0.98.

EXAMPLE 11

The procedure of Example 1 was repeated. However, 0.0058 part by weight of the co-catalyst of the formula

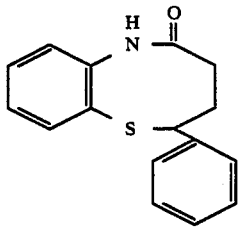

(2-phenyl-3,4-dihydro-2H-1,6-benzothiazocin-5(6H)-one) was added. The residual toluene content was 5.4% by weight and the o/p ratio 1.02.

EXAMPLE 12

The procedure of Example 1 was repeated. However, 0.0045 part by weight of the co-catalyst of the formula

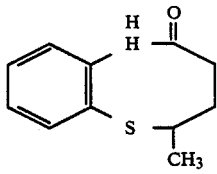

(2-methyl-3,4-dihydro-2H-1,6-benzothiazocin-5(6H)-one) was added. The residual toluene content was 8.9% by weight and the o/p ratio 1.10.

EXAMPLE 13

The procedure of Example 1 was repeated. However, 0.0112 part by weight of the co-catalyst of the formula

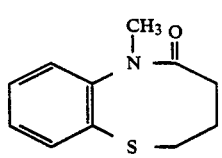

(6-methyl-3,4-dihydro-2H-1,6-benzothiazocin-56H)-one) was added. The residual toluene content was 3.5% by weight and the o/p ratio 1.03.

EXAMPLE 14

The procedure of Example 1 was repeated. However, only 0.0011 part by weight of the co-catalyst used there was used. The residual toluene content was 4.0% by weight and the o/p ratio 0.78.

EXAMPLE 15

The procedure of Example 1 was repeated. However, only 0.00055 part by weight of the co-catalyst used there was used. The residual toluene content was 4.4% by weight and the o/p ratio 0.79.

EXAMPLE 16

The procedure of Example 2 was repeated. However, only 0.0011 part by weight of the co-catalyst used there was used. The residual toluene content was 8.4% by weight and the o/p ratio 1.05.

EXAMPLE 17

The procedure of Example 13 was repeated. However, only 0.0045 part by weight of the co-catalyst used there was used. The residual toluene content was 7.3% by weight and the o/p ratio 1.06.

EXAMPLE 18

The procedure of Example 13 was repeated. However, only 0.0012 part by weight of the co-catalyst used there was used. The residual toluene content was 5.0% by weight and the o/p ratio 1.00.

EXAMPLE 19

The procedure of Example 9 was repeated. However, only 0.0012 part by weight of the co-catalyst used there was used. The residual toluene content was 5.4% by weight and the o/p ratio 1.10.

EXAMPLE 20

The procedure of Example 7 was repeated. However, only 0.0013 part by weight of the co-catalyst used there was used. The residual toluene content was 5.2% by weight and the o/p ratio was 0.88.

EXAMPLE 21 (COMPARATIVE EXAMPLE)

0.07 part by weight of $FeCl_3$ and 0.29 part by weight of the phenoxathiine derivative prepared by the procedure of EP 0,173,222 were dissolved in 100 parts by weight of toluene. About 94 mol-% of chlorine, relative to toluene, were introduced in the form of a gas with stirring at 50° C. The residual toluene content was 7.9% and the o/p ratio 0.88.

EXAMPLE 22 (COMPARATIVE EXAMPLE)

The procedure of Example 21 was repeated. 0.0175 part by weight of $FeCl_3$ and 0.008 part by weight of the phenoxathiine derivative prepared by the procedure of EP 0,173,222 were dissolved in 100 parts by weight of toluene. About 94 mol-% of $Cl_2$, relative to toluene, were introduced in the form of a gas with stirring at 50° C. The residual toluene content was 6.4% by weight and the o/p ratio 1.26.

EXAMPLE 23 (COMPARATIVE EXAMPLE)

The procedure of Example 21 was repeated. 0.0175 part by weight of $FeCl_3$ and 0.0065 part by weight of the co-catalyst of the formula

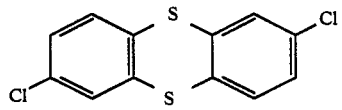

(2,7-dichlorothianthrene) mentioned in Example 4 of U.S. Pat. No. 4,031,147 were dissolved in 100 parts by weight of toluene. The mixture was heated to 50° C., and about 94 mol-% of $Cl_2$, relative to toluene, were introduced in the form of a gas with stirring. The residual toluene content was 6.7% by weight and the o/p ratio 1.55.

What is claimed is:

1. A process for the ring chlorination of an aromatic hydrocarbon of the formula

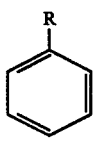

in which

R denotes straight-chain or branched $C_1$-$C_{12}$-alkyl or $C_3$-$C_8$-cycloalkyl, wherein said chlorination is conducted with chlorine or a chlorine-releasing substance in liquid phase and in the presence of at least one Friedel-Crafts catalyst and in the presence of at least one co-catalyst, wherein said at least one co-catalyst is a 1,6-benzothiazocin.

2. The process of claim 1, wherein said 1,6-benzothiazocin has the following formula

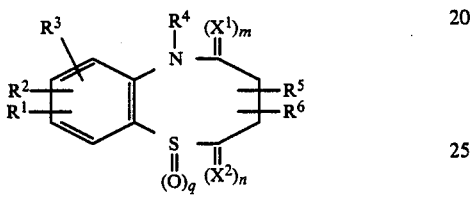

in which $R^1$ and $R^2$, independently of one another, denote hydrogen, hydroxyl, amino, cyano, halogen, nitro, alkylsulphonyl, phenylsulphonyl, alkylsulphoxyl, phenylsulphoxyl, tosyl, mercapto, carboxyl, halocarbonyl, carboxyamide, alkoxycarbonyl, thiocarboxyamide, alkyl, aryl, heteroaryl, alkoxy, aryloxy, heteroaryloxy, acyloxy, alkylthio, arylthio, heteroarylthio, acylthio, acyl, thioacyl or acylamino, $R^3$ stands for hydrogen or chlorine or can further form a fused saturated, unsaturated or aromatic isocyclic or heterocyclic 5- to 8-membered ring with one of the radicals $R^1$ to $R^2$ and together with the substituted carbon atoms, $R^4$ denotes, alkyl, aryl, heteroaryl, acyl, thioacyl, halocarbonyl or alkoxycarbonyl, $X^1$ and $X^2$, independently of one another, stand for oxygen, sulphur or $R^7$-substituted nitrogen, $R^7$ denotes alkyl, aryl, heteroaryl, acyl, thioacyl halocarbonyl or alkoxycarbonyl, m, n and q, independently of one another, are 0 or 1 and $R^5$ and $R^6$, independently of one another, can be located on one or two of the carbon atoms between the S and N atom in the 8-membered ring, unless these carbon atoms are occupied by $X^1$ or $X^2$, and denote hydrogen, hydroxyl, amino, cyano, halogen, nitro, alkylsulphonyl, phenylsulphonyl, alkylsulphoxyl, phenylsulphoxyl, tosyl, mercapto, carboxyl, halocarbonyl, carboxyamide, alkoxycarbonyl, thiocarboxyamide, alkyl, aryl, heteroaryl, alkoxy, aryloxy, heteroaryloxy, acyloxy, alkylthio, arylthio, heteroarylthio, acylthio, acyl, thioacyl or acylamino, where in the case of vicinal substitution they can also form a saturated, unsaturated or aromatic isocyclic or heterocyclic 5- to 8-membered ring with the substituted carbon atoms and where furthermore they can denote doubly bound oxygen or sulphur.

3. The process of claim 2, wherein the 1,6-benzothiazocin co-catalyst is of the formula

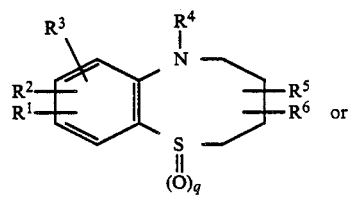

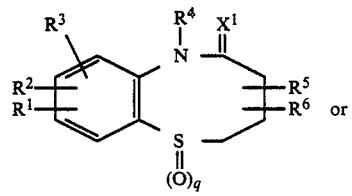

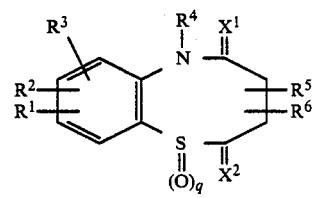

4. The process of claim 3, wherein the 1,6-benzothiazocin co-catalysts is of the formula

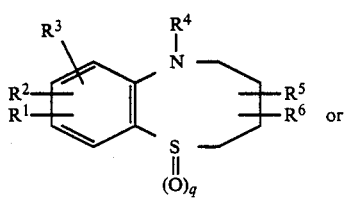

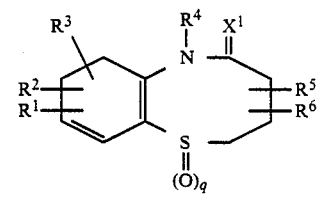

5. The process of claim 4, wherein the 1,6-benzothiazocin co-catalysts is of the formula

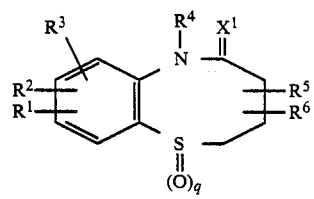

6. The process according to claim 2, where q is zero.

7. The process of claim 2, wherein said 1,6-benzothiazocin co-catalyst is of the formula

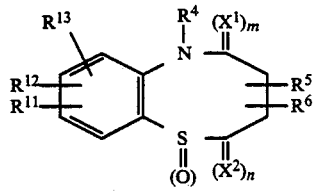

wherein
- $R^{11}$ and $R^{12}$, independently of one another, denote hydrogen, halogen, nitro, alkyl, aryl, alkoxy, aryloxy, acyloxy, alkylthio, arylthio, acyl or thioacyl and
- $R^{13}$ stands for hydrogen or chlorine or furthermore can form a fused, saturated, isocyclic 5- to 7-membered ring or a fused benzene ring with one of the radicals $R^{11}$ or $R^{12}$ and together with the substituted carbon atoms.

8. The process of claim 7, wherein said 1,6-benzothiazocin co-catalyst is of the formula

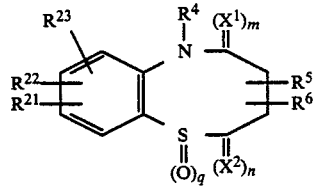

wherein
- $R^{21}$ and $R^{22}$, independently of one another, denote hydrogen, $C_1$–$C_4$-alkyl, $C_1$–$C_4$-alkoxy, fluorine or chlorine and
- $R^{23}$ stands for hydrogen or chlorine or furthermore can form a fused cyclopentane, cyclohexane or benzene ring with one of the radicals $R^{21}$ and $R^{22}$ and together with the substituted carbon atoms.

9. The process of claim 2, wherein the 1,6-benzothiazocin co-catalyst is of the formula

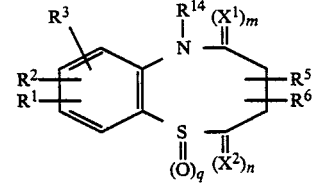

wherein $R^{14}$ denotes hydrogen, $C_1$–$C_4$-alkyl, phenyl, $C_1$–$C_4$-acyl or $C_2$–$C_4$-alkoxycarbonyl.

10. The process of claim 2, wherein the 1,6-benzothiazocin co-catalyst is of the formula

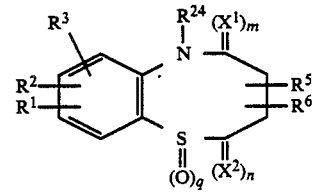

wherein
- $R^{24}$ denotes hydrogen, $C_1$–$C_2$-alkyl, benzyl, phenyl, acetyl, trifluoroacetyl, chloroacetyl, chlorocarbonyl or propionyl.

11. The process of claim 2, wherein the 1,6-benzothiazocin co-catalyst is of the formula

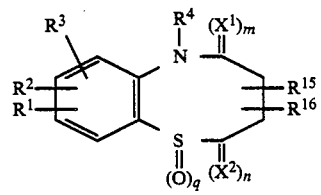

wherein $R^{15}$ and $R^{16}$ denote hydrogen, $C_1$–$C_4$-alkyl, $C_1$–$C_4$-alkoxy, $C_1$–$C_4$-acyl, phenyl, fluorine or chlorine and where in the case of vicinal substitution both radicals can furthermore form a cyclopentane, cyclohexane or benzene ring together with the substituted carbon atoms.

12. The process of claim 1, wherein the amount of co-catalyst used is 0.0001 to 0.5% by weight, relative to the aromatic hydrocarbon.

13. The process of claim 12, wherein the amount of co-catalyst used is 0.0005 to 0.1% by weight, relative to the aromatic hydrocarbon.

14. The process of claim 13, wherein the amount of co-catalyst used is 0.0005 to 0.0075 by weight, relative to the aromatic hydrocarbon.

15. The process of claim 1, wherein the ring chlorination is carried out to a temperature of 0°–100° C.

16. The process of claim 15, wherein the ring chlorination is carried out at a temperature of 20°–80° C.

17. The process of claim 1, wherein the chlorine or a chlorine-releasing substance is used in an amount of 0.8–1.1 mole per mole of the aromatic hydrocarbon.

18. The process of claim 1, wherein the Friedel-Crafts catalyst is selected from the group consisting of antimony chlorides, aluminum chlorides, iron, iron oxides, iron sulphides, iron carbonyls, iron(III)chloride and mixtures thereof.

19. The process of claim 18, wherein the Friedel-Crafts catalyst is iron(III)chloride.

20. The process of claim 1, wherein the Friedel-Crafts catalyst is used in an amount of 0.001–0.5% by weight, relative to the aromatic hydrocarbon used.

* * * * *